United States Patent
Chien et al.

(10) Patent No.: US 10,295,469 B2
(45) Date of Patent: May 21, 2019

(54) TEMPORAL FOCUSING-BASED MULTIPHOTON EXCITATION FLUORESCENCE MICROSCOPY SYSTEM CAPABLE OF TUNABLE-WAVELENGTH EXCITATION AND EXCITATION WAVELENGTH SELECTION MODULE THEREOF

(71) Applicant: NATIONAL CENTRAL UNIVERSITY, Taoyuan (TW)

(72) Inventors: Fan-Ching Chien, Taoyuan (TW); Chi-Hsiang Lien, Taoyuan (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 0 days.

(21) Appl. No.: 15/897,446

(22) Filed: Feb. 15, 2018

(65) Prior Publication Data
US 2018/0335384 A1    Nov. 22, 2018

(30) Foreign Application Priority Data

May 22, 2017   (TW) .............................. 106116835 A (51) Int. Cl.
*G01N 21/64*   (2006.01)
*G02B 5/18*    (2006.01)
(Continued)

(52) U.S. Cl.
CPC ........... *G01N 21/6458* (2013.01); *G02B 5/18* (2013.01); *G02B 21/0076* (2013.01);
(Continued)

(58) Field of Classification Search
CPC .... G01N 21/255; G01N 21/76; G01N 21/645; G01N 2201/061; G01N 21/6458;
(Continued)

(56) References Cited

U.S. PATENT DOCUMENTS

| 6,452,710 | B1* | 9/2002 | Hiraga | G02F 1/293 359/244 |
| 9,784,670 | B1* | 10/2017 | Mohan | G01N 21/255 |
| 2005/0265403 | A1* | 12/2005 | Anderson | H01S 5/143 372/20 |

* cited by examiner

*Primary Examiner* — Kiho Kim
(74) *Attorney, Agent, or Firm* — Juan Carlos A. Marquez; Marquez IP Law Office, PLLC (57) ABSTRACT

The invention provides a temporal focusing-based multiphoton excitation fluorescence microscopy system capable of tunable-wavelength excitation and an excitation wavelength selection module thereof. The temporal focusing-based multiphoton excitation fluorescence microscopy system comprises: an excitation light generating module for generating excitation light; an excitation wavelength selection module for generating reflected light having a predetermined output angle in accordance with the wavelength of the excitation light and generating detecting excitation light through a diffraction unit; and a fluorescent microscope. With the practice of the present invention, the wavelength of the excitation light can be changed by the excitation wavelength selection module in real time to excite different fluorophores with the corresponding maximum multiphoton absorption wavelengths, so as to obtain better fluorescent signals and improve the image quality of the temporal focusing-based multiphoton excitation fluorescence microscope system.

4 Claims, 5 Drawing Sheets

(51) Int. Cl.
*G02B 21/00* (2006.01)
*G02B 27/10* (2006.01)

(52) U.S. Cl.
CPC ....... *G02B 21/0084* (2013.01); *G02B 27/104* (2013.01); *G02B 27/1086* (2013.01)

(58) Field of Classification Search
CPC . G02B 5/04; G02B 7/182; G02B 5/08; G02B 27/42; G02B 5/18; G02B 21/0076; G02B 21/0084; G02B 27/104; G02B 27/1086
See application file for complete search history.

TEMPORAL FOCUSING-BASED MULTIPHOTON EXCITATION FLUORESCENCE MICROSCOPY SYSTEM CAPABLE OF TUNABLE-WAVELENGTH EXCITATION AND EXCITATION WAVELENGTH SELECTION MODULE THEREOF

BACKGROUND OF THE INVENTION

1. Technical Field

The present invention relates to a temporal focusing-based multiphoton excitation fluorescence microscopy system capable of tunable-wavelength excitation and an excitation wavelength selection module thereof. More particularly, the invention relates to a fluorescence microscopy system for examining diverse bio-tissues and the configuration of the system's wavelength selection module.

2. Description of Related Art

Multiphoton excitation (MPE) fluorescence microscopes can be used in the biomedical field. Generally, the wavelength of the excitation light is selected according to the fluorescent dye with which to label a specimen, and the labeled specimen is scanned to obtain fluorescence images for display and analysis. In multifluorophore imaging, however, MPE fluorescence microscopy with a fixed-wavelength pulse laser illumination configuration is insufficient to perform efficient excitation of fluorophores with different two-photon absorption spectra.

Many fluorescence proteins and fluorophores used in biomedical studies have demonstrated the specific spectra of multiphoton absorption. The highly effective multiphoton excitation of fluorophores provides superior signal-to-noise ratio (SNR) MPE imaging, where SNR is critical to the imaging depth of three-dimensional biospecimens. Although fluorescent excitation of two different fluorophores with overlapping two-photon absorption spectra can be achieved using conventional MPE fluorescence microscopes with a single excitation wavelength, the selection of fluorophores for biomedical applications is restricted.

In spatial-focusing-only MPE microscopy where galvo scanners are used to map MPE fluorescence images, matching the maximum multiphoton absorption wavelengths of different fluorophores is straightforward through adjustment of the incident wavelength of ultrafast pulse lasers. In a temporal focusing-based AVE fluorescence microscopy system, however, adjusting the incident wavelength in real time to obtain the optimum efficiency of MPE for higher image quality is difficult because of the use of a diffraction device, which separates the frequencies of incident pulses at different diffraction angles.

BRIEF SUMMARY OF THE INVENTION

The present invention provides a temporal focusing-based MPE fluorescence microscopy system featuring tunable-wavelength excitation and its excitation wavelength selection module. The invention is intended mainly to improve the imaging quality of the conventional temporal focusing-based MPE fluorescence microscopy systems.

The present invention provides a temporal focusing-based multiphoton excitation (MPE) fluorescence microscopy system capable of tunable-wavelength excitation, comprising: an excitation wavelength generation module for generating excitation light of a predetermined wavelength and thereby forming an optical path; an excitation wavelength selection module comprising: an angular adjustment unit which is a reflection device configured to rotate at a fixed point in order to reflect the excitation light; a control unit for driving the angular adjustment unit according to the predetermined wavelength of the excitation light in order for the excitation light to generate reflected excitation light having a predetermined output angle; and a diffraction unit for receiving the reflected excitation light and generating detecting excitation light; and a fluorescence microscope with an illuminative optical lens set having an incident end configured for receiving the detecting excitation light in order to examine a to-be-examined object.

Implementation of the invention at least produces the following effects:

1. The excitation wavelength selection module enables adjustment of the excitation wavelength in real time.

2. Dynamic adjustment of the detecting light source in real time can lead to higher image quality than achievable in the prior art.

The features and advantages of the present invention are detailed hereinafter with reference to the preferred embodiments. The detailed description is intended to enable a person skilled in the art to gain insight into the technical contents disclosed herein and implement the present invention accordingly. In particular, a person skilled in the art can easily understand the objects and advantages of the present invention by referring to the disclosure of the specification, the claims, and the accompanying drawings.

DETAILED DESCRIPTION OF THE INVENTION

Figure 1:
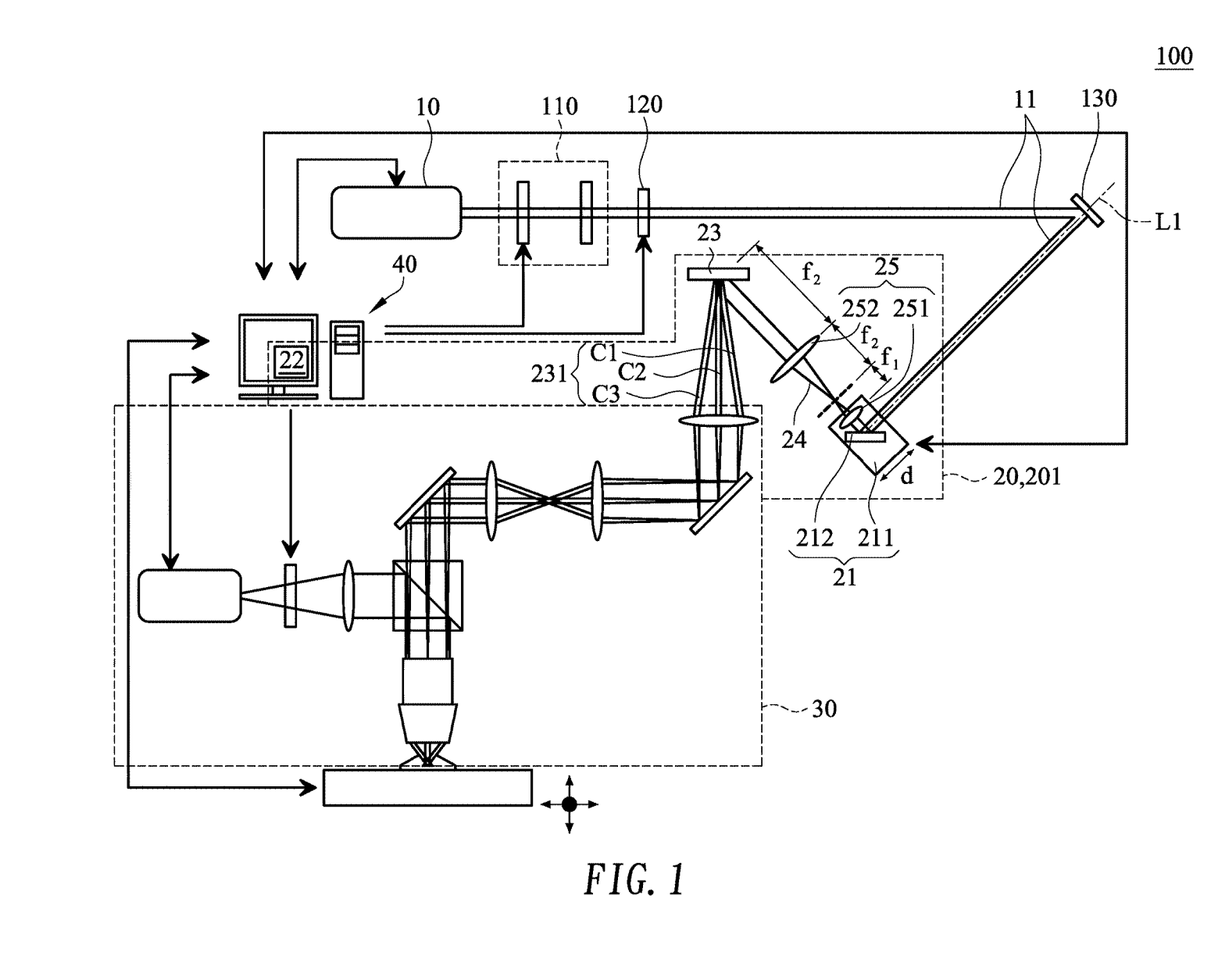
FIG. 1 shows an embodiment of a fluorescence microscopy system with an obliquely movable excitation wavelength selection module according to the present invention.
Figure 2:
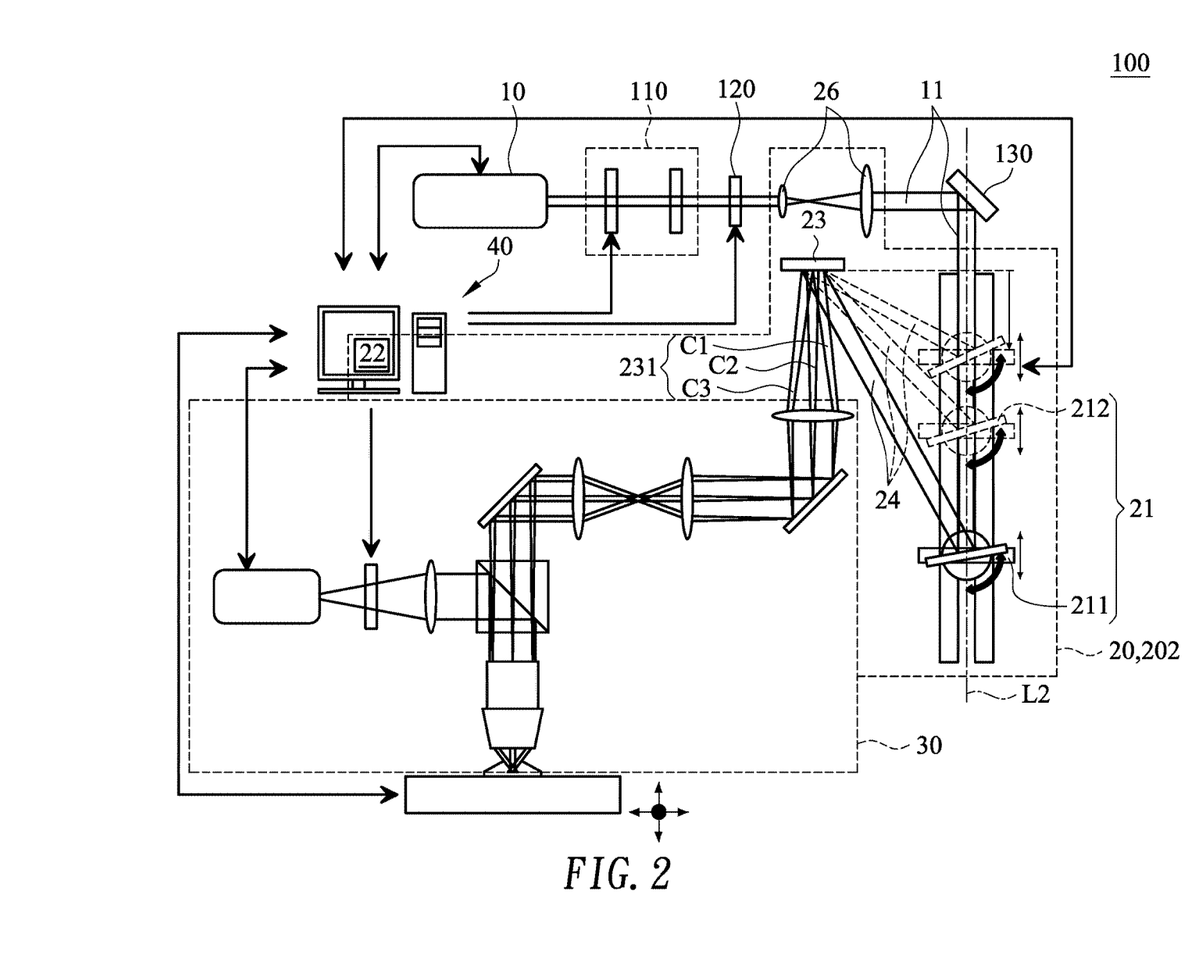
FIG. 2 shows an embodiment of a fluorescence microscopy system with a vertically movable excitation wavelength selection module according to the present invention.
Figure 3:
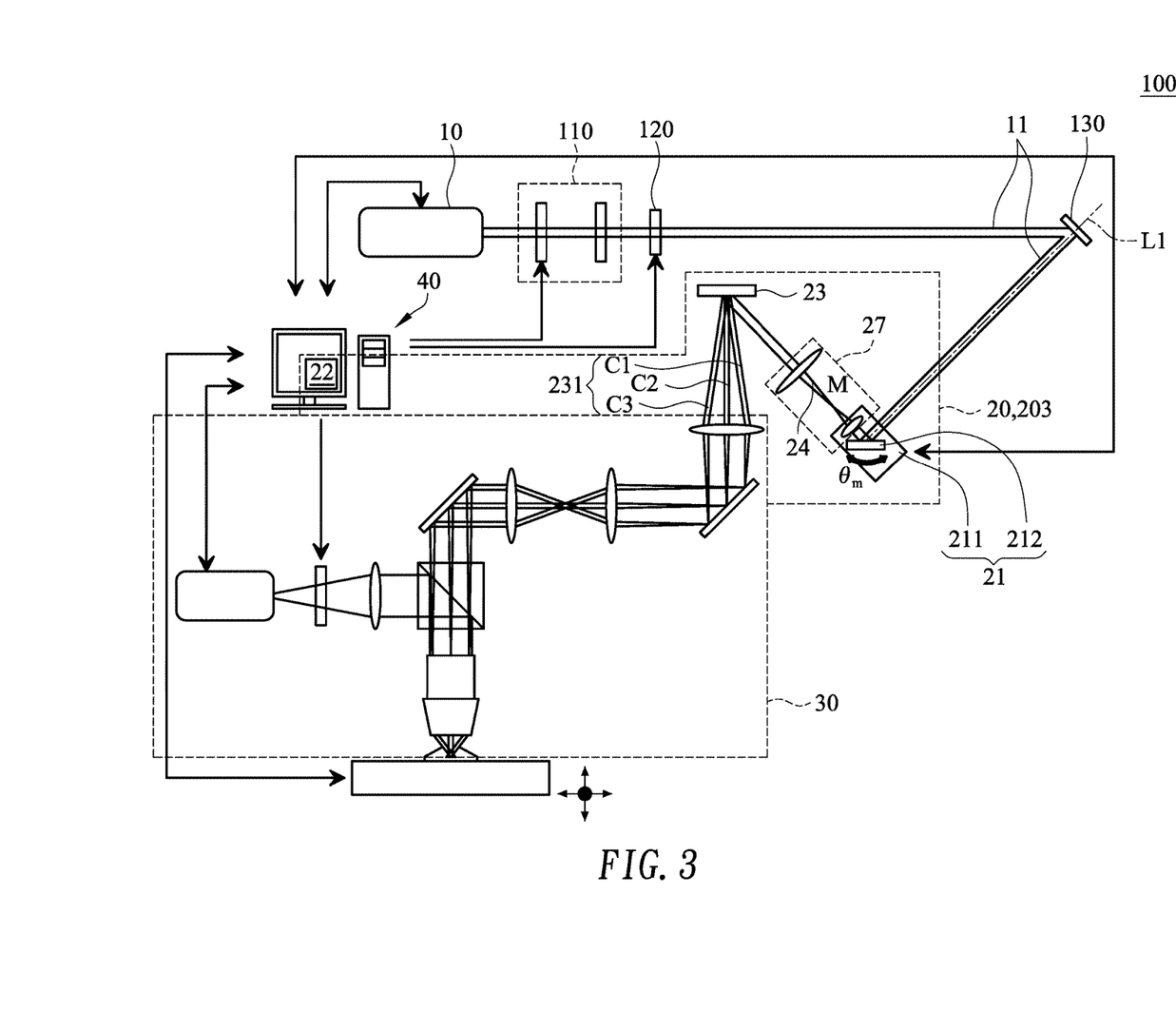
FIG. 3 shows an embodiment of a fluorescence microscopy system with a rotatably adjustable excitation wavelength selection module according to the present invention.

Referring to FIG. 1, FIG. 2, and FIG. 3 for an embodiment of the present invention, a temporal focusing-based MPE fluorescence microscopy system 100 capable of tunable-wavelength excitation includes an excitation light generation module 10, an excitation wavelength selection module 20, and a fluorescence microscope 30.

The excitation light generation module 10 uses a laser to generate the excitation light 11 required for examining a biospecimen. The wavelength of the excitation light 11 can be selected according to the biospecimen to be examined with the fluorescence microscope 30, in order for the excitation light 11 to have a specific wavelength $\lambda$ suitable for illumination. Once generated, and during system operation, the excitation light 11 forms an optical path.

To meet the requirements of different illumination light sources, the output end of the excitation light generation module 10 may be provided with a light power regulator 110 for regulating the output power of the excitation light 11 and/or with a shutter 120. The light power regulator 110 can be used to adjust light intensity while the shutter 120 serves as a switch to block, or allow passage of, the excitation light.

The excitation wavelength selection module 20, or more particularly its diffraction unit 23, allows one who desires to examine a biospecimen to rapidly select a specific wavelength λ for the excitation light 11 that is suitable for the examination. The excitation wavelength selection module 20 essentially includes an angular adjustment unit 21 and a control unit 22 in addition to the diffraction unit 23.

The angular adjustment unit 21 mainly includes a displacement device 211 and a reflection device 212. The displacement device 211, composed for example of a slide rail and a drive motor for driving the slide rail, is provided in and can be moved along the optical path of the excitation light 11. The reflection device 212 is, for example, a mirror coupled with a rotation motor for effecting a change in angle of the mirror.

The reflection device 212 is provided on the displacement device 211 to reflect the excitation light 11 and thereby generate reflected excitation light 24. Since the optical path of the excitation light 11 is fixed, a change in position of the displacement device 211 or a change in angle of the reflection device 212 alters the focus or output angle of the reflected excitation light 24 generated by reflecting the excitation light 11.

Figure 4:
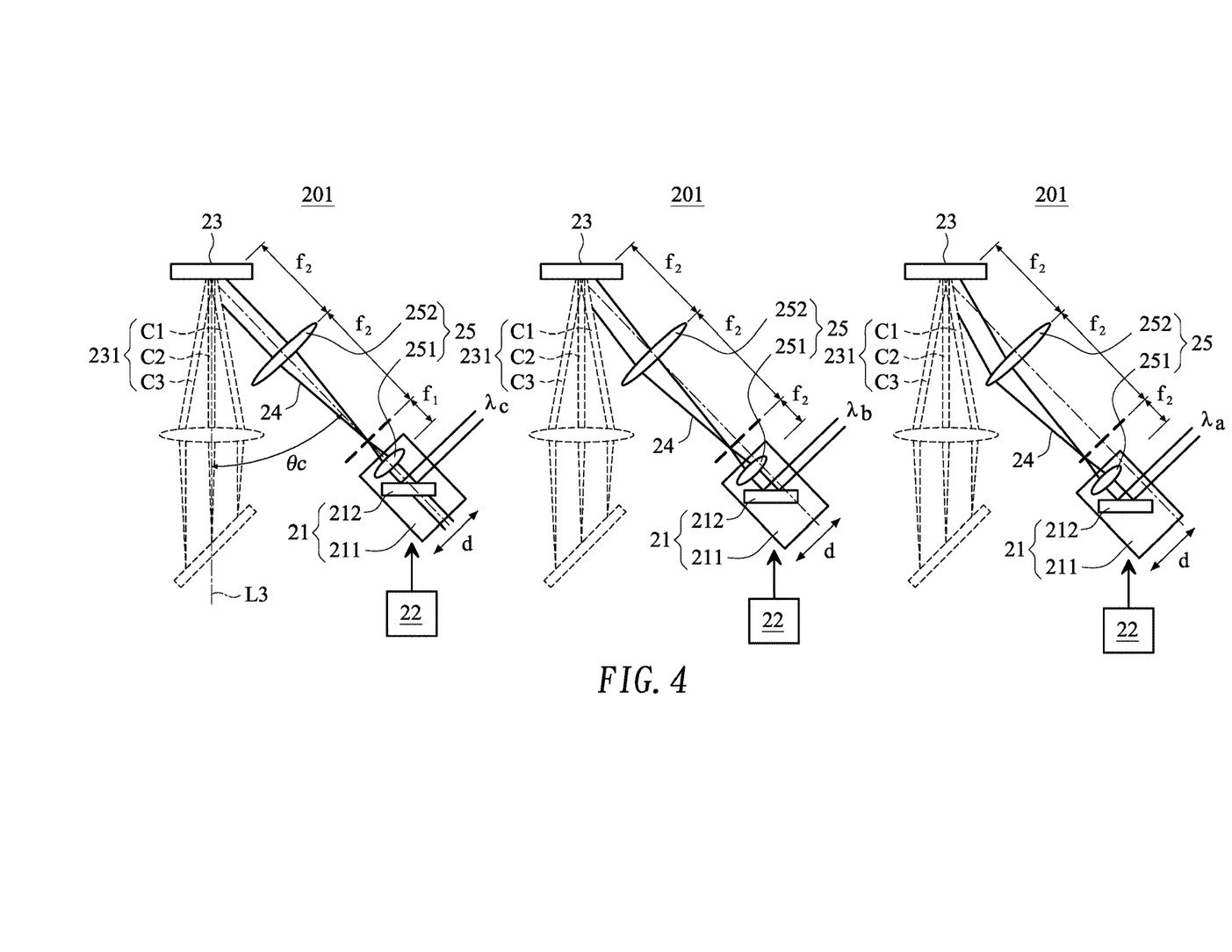
FIG. 4 shows how the wavelength selection module in FIG. 1 is moved along a sloping line.
Figure 5:
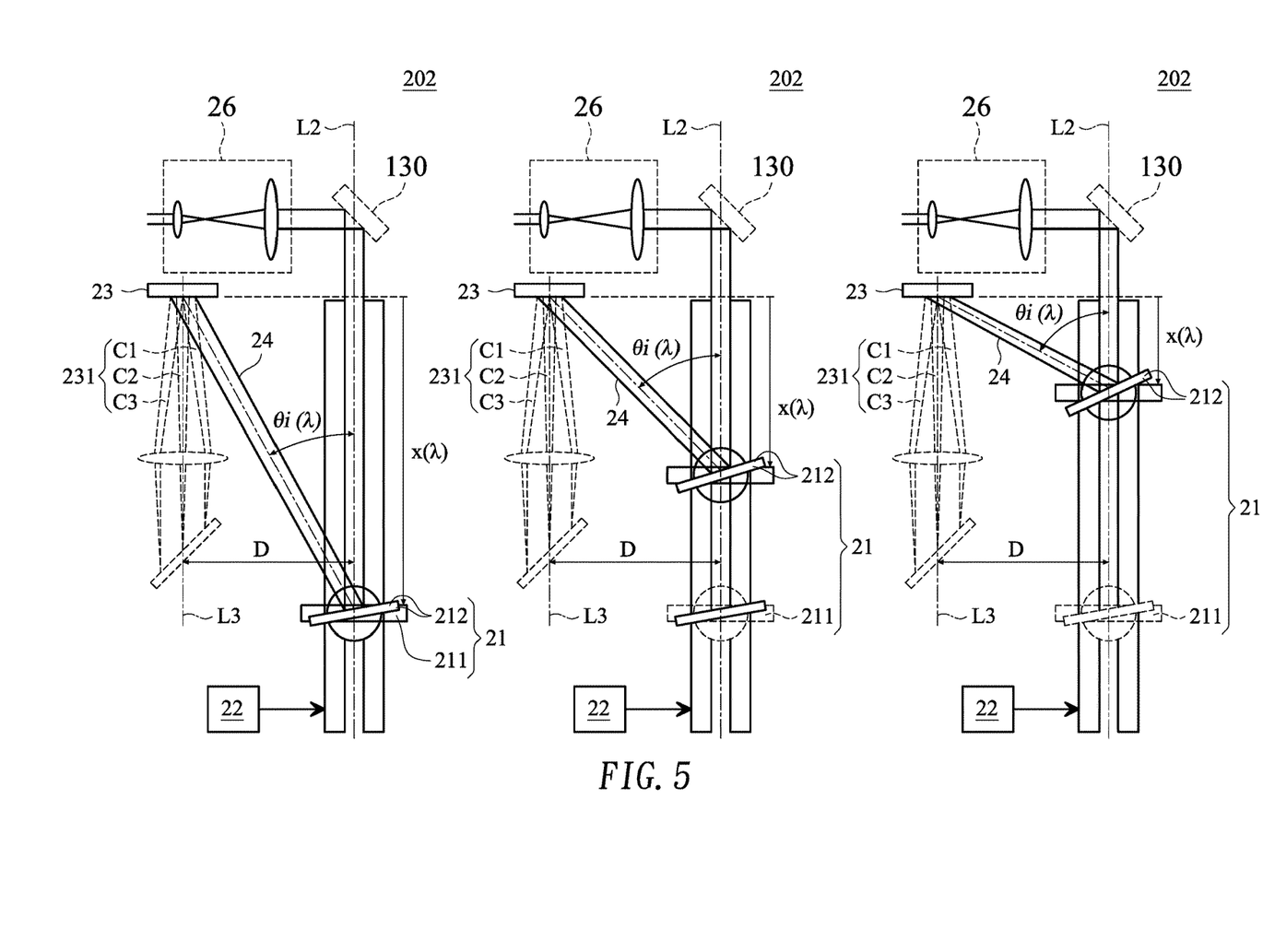
FIG. 5 shows how the wavelength selection module in FIG. 2 is moved along a vertical line.

Referring to FIG. 3, FIG. 4, and FIG. 5. the excitation wavelength selection module 20 can be categorized by its mode of movement as an obliquely movable excitation wavelength selection module 201 configured for moving along a sloping line L1, a vertically movable excitation wavelength selection module 202 configured for moving along a vertical line L2, or a rotatably adjustable excitation wavelength selection module 203. The sloping line L1 and the vertical line L2 are named after the direction of the optical path formed by a path device 130 reflecting the excitation light 11. It should be understood, however, that the excitation light 11 may be projected directly to the excitation wavelength selection module 20 without being reflected by the path device 130.

The diffraction unit 23 in this embodiment is an optical grating, whose diffraction equation can be expressed as:

$$m\lambda = a(\sin \theta_i + \sin \theta_m) \quad \text{(Eq. 1)}$$

where: m is an integer indicating the order of diffraction; λ is the central wavelength of the excitation light 11; a is the effective pitch of the periodic structures of the diffraction unit 23, or an optical grating: $\theta_i$ is the angle of incidence of the reflected excitation light 24 on the optical grating 23, hereinafter also referred to as the angle of incidence of the reflected excitation light for short; and $\theta_m$ is the angle of diffraction of the $m^{th}$ order diffraction light.

The excitation wavelength selection module 20 shown in FIG. 1 and FIG. 4 is the obliquely movable excitation wavelength selection module 201, in which the displacement device 211 is provided in a sloping optical path section of the excitation light 11 and can be moved obliquely along the sloping optical path section, and in which the reflection device 212 is provided on the displacement device 211 to reflect the excitation light 11. That is to say, the angular adjustment unit 21 is configured to be moved along the sloping line L1.

FIG. 4 shows positions of the angular adjustment unit 21 that correspond respectively to three specific wavelengths λ of the excitation light 11, the three wavelengths being identified as central wavelengths $\lambda_a$, $\lambda_b$, and $\lambda_c$, wherein $\lambda_a$=770 nm, $\lambda_b$=850 nm, and $\lambda_c$=920 nm. The reflection end of the reflection device 212 is provided with a first beam-expanding device 251. The first beam-expanding device 251 and the reflection device 212 are configured to be moved together in the same direction and at the same angle.

A second beam-expanding device 252 is fixedly provided at the incident end of the diffraction unit 23. The second beam-expanding device 252 and the diffraction unit 23 are spaced apart by a fixed distance and are arranged at a fixed angle with respect to each other. The first beam-expanding device 251 and the second beam-expanding device 252 jointly form a first beam expander 25. The first beam expander 25 is used to receive, and expand the beam of, the reflected excitation light.

In terms of system setup for this configuration, the direction of light diffracted to the first order (m=1) is defined as 0° (i.e., $\theta_1$=0°) to ensure that, despite changes in wavelength, the beam of the excitation light 11 will be spatially dispersed with its central-frequency component travelling along the optical path of the system. The angle of incidence $\theta_i$ of the reflected excitation light must be adjusted for different central wavelengths of the laser according to the diffraction equation and therefore can be rewritten as:

$$\theta_i(\lambda) = \sin^{-1}(\lambda/a) \quad \text{(Eq. 2)}.$$

In addition, the relationship between the angular variation Ø of the output beam of the second beam-expanding device 252 and the shifting distance d of the first beam-expanding device 251 can be expressed as:

$$\varnothing = \sin^{-1}(d/f_2) \quad \text{(Eq. 3)}$$

where $f_2$ is the focal length of the second beam-expanding device 252. In this embodiment, the initial settings of the excitation light include a central wavelength of 920 nm and incidence on the diffraction unit 23 at an angle $\theta_c$ with respect to the central axis L3 of the detecting excitation light 231, By combining Eq. 2 and Eq. 3, the shifting distance d of the angular adjustment unit 21 corresponding to the central wavelength $\lambda_i$ of the excitation light 11 can be expressed as:

$$d = f_2 \sin[\sin^{-1}(\lambda_i/a) - \sin^{-1}(920 \text{ nm}/a)] = f_2 \sin[\sin^{-1}(\lambda_i/a) - \theta_c] \quad \text{(Eq. 4)}.$$

The excitation wavelength selection module 20 shown in FIG. 2 and FIG. 5 is the vertically movable excitation wavelength selection module 202, in which the displacement device 211 is arranged for vertical movement so that the angular adjustment unit 21 is movable along the vertical line L2. The first beam expander 25, therefore, can be dispensed with, but a second beam expander 26 must be provided in the optical path of the excitation light 11 at a position where the excitation light 11 has yet to reach the reflection device 212.

In this configuration, the reflection device 212 can be moved along with and rotated with respect to the displacement device 211 in order for the angular adjustment unit 21 to change the angle of incidence of the excitation light 11 on the diffraction unit 23. The angle of reflection corresponds to the angle of incidence through Eq. 1 so that the illuminated position on the diffraction unit 23 remains unchanged regardless of variation of the central wavelength of the excitation light 11. Based on the geometric settings for specific wavelengths, the central axis L3 of the detecting, excitation light 231 is spaced apart from the vertical line L2, along which the reflection device 212 is moved, by a distance D; in other words, the horizontal distance between the central axis L3 and the vertical line L2 is D. Thus, the angle of incidence $\theta_i(\lambda)$ of the reflected excitation light can be expressed as:

$$\theta_i(\lambda)=\sin^{-1}(\lambda/a)=\tan^{-1}(D/x(\lambda)) \quad \text{(Eq. 5)}$$

where $x(\lambda)$ is the linear displacement of the displacement device 211, i.e., the vertical distance from the plane of the diffraction unit 23 that receives the excitation light 11 to the displacement device 211, which distance can be expressed as:

$$x(\lambda)=[\sqrt{((a^2/\lambda^2)-1)}]D \quad \text{(Eq. 6)}.$$

The rotatably adjustable excitation wavelength selection module 203 shown in FIG. 3 is based on the following theory. To carry out temporal focusing, the diffraction unit 23 must be able to perform spatial division of the frequencies of the ultrashort pulses emitted by the ultrafast laser of the excitation light generation module 10. Therefore, to use an optical grating as the diffraction unit 23, the preliminary setup may include a diffraction grating with a groove density of 1,200 lines/mm used together with single-wavelength (780 nm) excitation light whose diffraction angle is about 70°, as determined by the diffraction equation of Eq. 1.

Eq. 1 signifies that irradiating an optical grating with plane waves of different wavelengths results in different diffraction angles and different levels of diffraction efficiency. In a temporal focusing-based optical system, the focal plane of the objective lens and the plane of the diffraction grating are conjugate planes. If the plane of the diffraction grating is not adjusted to a position where light diffracted to the first order is perpendicular to the grating plane (i.e., allowing the diffraction grating to have a tilt angle), there will be a corresponding tilt angle between the excitation plane of the excited specimen and the imaging plane such that the image obtained is blurred.

The excitation wavelength selection module 20 shown in FIG. 3 is the rotatably adjustable excitation wavelength selection module 203, in which the angular adjustment unit 21 is a reflection device 212 configured to rotate at a fixed point in order to reflect the excitation light 11. In addition, a third beam expander 27 is provided downstream of the reflection end of the reflection device 212. More specifically, the excitation wavelength selection module 203 can be rotated at a fixed point according to the wavelength of the excitation light 11 so as to adjust the angle of incidence $\theta_i$ of the reflected excitation light, allowing light diffracted to the first order to propagate along the central axis L3 of the detecting excitation light 231 ($\theta_{m=1}=0°$). The required angle of incidence can be achieved through a commercially available optical grating with a groove density of 830 or 600 lines/mm and laser light whose central wavelength ranges from 700 nm to 1000 nm.

Based on the required diffraction angle, temporal focusing-based MPE can be carried out with excitation light of different wavelengths by means of a scan mirror assembly and an optical lens set of the microscope that are configured to adjust the angle of incidence of the reflected excitation light. Besides, in order for the rotatably adjustable excitation wavelength selection module 203 to adjust the angle of incidence of the reflected excitation light effectively, a motor call be used to rotate the scan mirror assembly so that the reflected laser light enters the third beam expander 27 and strikes the same spot on the diffraction unit 23 as collimated light at different angles. The relationship between the excitation wavelength $\lambda_i$ and the angle of rotation $\theta_m(\lambda)$ of the reflection device 212 is as follows:

$$\theta_m(\lambda_i)=\tan^{-1}[M\times\tan(\sin^{-1}(\lambda_i/a)-\theta_c)] \quad \text{(Eq. 7)}$$

where: M is the magnification of the third beam expander 27, and $\theta_c$ is the angle of incidence corresponding to the initial wavelength of the excitation light, such as 920 nm.

The control unit 22 is applied to the excitation wavelength selection module (which may fall within any of the foregoing three categories) to control and operate the angular adjustment unit 21 systematically and effectively. The control unit 22 reads the central wavelength of the excitation light 11 generated by the excitation light generation module 10 and drives the angular adjustment unit 21 (by moving the displacement device 211 and/or rotating the reflection device 212) according to the central wavelength to ensure that the reflected excitation light 24 derived from the excitation light 11 can be focused at a specific point or has a specific output angle.

The diffraction unit 23 is applied to the excitation wavelength selection module (which may fall within any of the foregoing three categories) to selectively receive the reflected excitation light 24 at a specific angle of incidence corresponding to the excitation wavelength selection module 20 and divide the reflected excitation light 24 into first color light C1 (e.g., red light), second color light C2 (e.g., grass green light), third color light C3 (e.g., cyan light), and so on as the detecting excitation light 231, which provides illumination for the fluorescence microscope 30. The diffraction unit 23 may be a diffraction grating or a digital micromirror device. When the central wavelength of the excitation light 11 generated by the excitation light generation module 10 is changed, the illumination angle of the reflected excitation light 24 can be changed accordingly to maintain the illuminated position on the diffraction unit 23, the diffraction angle, and consequently the optical path downstream of the diffraction unit 23, allowing rapid adjustment of the excitation wavelength to be achieved.

The fluorescence microscope 30 requires an illumination light source when used to examine a biospecimen; hence, the incident end of the illuminative optical lens set of the fluorescence microscope 30 is configured to receive the detecting excitation light 231. The detecting excitation light 231 passes through a series of optical lenses in the fluorescence microscope 30 to enable examination of a to-be-examined object.

While the fluorescence microscopy system is in use, an operator can adjust the detecting light source dynamically in real time based on the state of the image observed, with a view to higher image quality. Furthermore, a computer 40 can be used to control the excitation light generation module 10, the excitation wavelength selection module 20, the fluorescence microscope 30, and the image processing process that follows.

The embodiments described above are intended only to demonstrate the technical concept and features of the present invention so as to enable a person skilled in the art to understand and implement the contents disclosed herein. It is understood that the disclosed embodiments are not to limit the scope of the present invention. Therefore, all equivalent changes or modifications based on the concept of the present invention should be encompassed by the appended claims.

What is claimed is:

1. A temporal focusing-based multiphoton excitation (MPE) fluorescence microscopy system capable of tunable-wavelength excitation, comprising:
    an excitation wavelength generation module for generating excitation light of a predetermined wavelength and thereby forming an optical path;
    an excitation wavelength selection module comprising:
        an angular adjustment unit which is a reflection device configured to rotate at a fixed point in order to reflect the excitation light;

a control unit for driving the angular adjustment unit according to the predetermined wavelength of the excitation light in order for the excitation light to generate reflected excitation light having a predetermined output angle; and a diffraction unit for receiving the reflected excitation light and generating detecting excitation light; and a fluorescence microscope with an illuminative optical lens set having an incident end configured for receiving the detecting excitation light in order to examine a to-be-examined object;

wherein the angular adjustment unit is rotatable at the fixed point according to the equation $\theta m(\lambda i)=\tan-1[M\times\tan(\sin-1(\lambda i/a)-\theta c)]$, and the temporal focusing-based MPE fluorescence microscopy system further comprises a third beam expander provided downstream of a reflection end of the reflection device, where: $\theta m(\lambda i)$ is an angle of rotation of the reflection device, M is a magnification of the third beam expander, $\lambda i$ is a central wavelength of the excitation light, a is an effective pitch of periodic structures of the diffraction unit, and $\theta c$ is an angle of incidence corresponding to an initial wavelength of the excitation light.

2. The temporal focusing-based MPE fluorescence microscopy system of claim 1, wherein the diffraction unit is a diffraction grating or a digital micromirror device.

3. The temporal focusing-based MPE fluorescence microscopy system of claim 1, wherein the excitation light generation module has an output end provided with a light power regulator.

4. The temporal focusing-based MPE fluorescence microscopy system of claim 1, further comprising a shutter provided between the excitation light generation module and the reflection device.

* * * * *